United States Patent
Bjorkesten et al.

(10) Patent No.: US 9,446,329 B2
(45) Date of Patent: Sep. 20, 2016

(54) PREPARATION OF LIQUID MIXTURES

(75) Inventors: Lennart Bjorkesten, Uppsala (SE);
Enrique Carredano, Uppsala (SE);
Gunnar Malmquist, Uppsala (SE);
Gustav Rodrigo, Uppsala (SE); Nils Stafstrom, Uppsala (SE)

(73) Assignee: GE Healthcare Bio-Sciences AB, Uppsala (SE)

(*) Notice: Subject to any disclaimer, the term of this patent is extended or adjusted under 35 U.S.C. 154(b) by 854 days.

(21) Appl. No.: 12/988,553

(22) PCT Filed: Apr. 20, 2009

(86) PCT No.: PCT/SE2009/050399
§ 371 (c)(1),
(2), (4) Date: Oct. 19, 2010

(87) PCT Pub. No.: WO2009/131524
PCT Pub. Date: Oct. 29, 2009

(65) Prior Publication Data
US 2011/0039712 A1 Feb. 17, 2011

(30) Foreign Application Priority Data

Apr. 21, 2008 (SE) .................... 08009151

(51) Int. Cl.
*G01N 30/34* (2006.01)
*B01D 15/12* (2006.01)
*B01D 15/16* (2006.01)
*B01D 15/36* (2006.01)

(52) U.S. Cl.
CPC ............. *B01D 15/12* (2013.01); *B01D 15/166* (2013.01); *B01D 15/361* (2013.01); *G01N 30/34* (2013.01); *G01N 2030/347* (2013.01)

(58) Field of Classification Search
None
See application file for complete search history.

(56) References Cited

U.S. PATENT DOCUMENTS

| | | | |
|---|---|---|---|
| 3,712,513 A | 1/1973 | Ashmead et al. | |
| 4,500,500 A * | 2/1985 | Paalman et al. | 423/224 |
| 5,112,949 A | 5/1992 | Vukovich | |
| 6,221,250 B1 | 4/2001 | Stafstrom | |
| 7,138,051 B2 | 11/2006 | De Lamotte | |
| 2005/0082228 A1 | 4/2005 | De Lamotte | |

FOREIGN PATENT DOCUMENTS

| | | |
|---|---|---|
| WO | WO 97/31692 | 9/1997 |
| WO | WO 2005/025726 | * 3/2005 |

OTHER PUBLICATIONS

Fredenslund et al 1975 AIChE Journal 21:1086-99.*
Abbas, Z., et al., Fluid Phase Equilibria, 260(2), 233-247 (2007).
Lu, X., et al., AIChE Journal, 39(9), 1527-1538 (1993).
Papaiconomou, N., et al., Physical Chemistry Chemical Physics, 4, 4435-4443 (2002).
Roy, L., et al., Journal of Solution Chemistry, 35(4), 551-566 (2006).
Lin, C.-L., et al., Fluid Phase Equilibria, 205(1), 69-88 (2003).
Guggenheim, E., et al., Journal of Physical Chemistry, 38(4) (1934) 533-541.
Kielland, J., Activity Coefficients of Ions in Aqueous Solutions, 59 (1937) 1675-1678.
Okamoto, H., et al., Pharmaceutical Research, 14(3) (1997) 299-302.

* cited by examiner

*Primary Examiner* — Christopher M Gross
(74) *Attorney, Agent, or Firm* — Wood IP LLC

(57) ABSTRACT

A method of determining the relative component proportions of at least one each of: a buffer; an acid or a base; a solvent; and optionally a salt, for providing a liquid mixture of pre-defined pH and ionic strength, wherein the relative component proportions are determined using the equation of Debye-Hückel, wherein the ion size parameter a in the Debye-Hückel equation is determined as the weighted mean ion size of all species contributing to the ionic strength of the liquid mixture, and wherein the ionic strength of each species is used as weighting parameter. The present method is also applicable in a method of providing a liquid mixture. Further there is provided a buffer preparation device.

9 Claims, 6 Drawing Sheets

Table 1

| Nr-Titr | Buffer | Titrant | pKa | dpKa/dT | konst | Shell pos | Shell neg | $N_{OK}$ | r.m.s. (Exp1-Exp2) | r.m.s. Calc-Exp1 (Guggenheim & Schindler) | r.m.s. Calc-Exp1 ("Buffalo") |
|---|---|---|---|---|---|---|---|---|---|---|---|
| 1-1 | 1-Methylpiperazine | HCl | 4.43, 9.01 | -0.015, -0.024 | 0.5 | 1.1 | 0.0 | 38 | 0.03(0) | 0.06 (4) | 0.05 (1) |
| 2-1 | Bis Tris | HCl | 6.46 | -0.017 | 0.5 | 4.0 | 0.0 | 8 | 0.04 (0) | 0.07 (3) | 0.03 (0) |
| 3-1 | Piperazine | HCl | 5.5, 9.81 | -0.015, -0.026 | 0.5 | 4.0 | 0.0 | 4 | 0.04 (0) | 0.08 (2) | 0.03 (0) |
| 4-1 | Tris | HCl | 8.07 | -0.028 | 0.5 | 4.0 | 0.0 | 8 | 0.04 (0) | 0.13 (6) | 0.05 (0) |
| 6-1 | Bistrispropane | HCl | 6.65, 9.0 | -0.026, -0.030 | 0.5 | 4.0 | 0.0 | 46 | No Exp2 | 0.17 (20) | 0.04 (1) |
| 7-1 | Na-Acetate | HCl | 4.76 | -0.0002 | 0.5 | 4.0 | 0.0 | 6 | 0.05 (2) | 0.08 (0) | 0.05 (0) |
| 7-3 | Na-Acetate | Acetic acid | 4.76 | -0.0002 | 0.5 | 4.0 | 0.0 | 10 | 0.02 (0) | 0.07 (0) | 0.04 (0) |
| 8-2 | Bicine | NaOH | 1.84, 8.33 | 0, -0.017 | 0.5 | 4.0 | 0.0 | 20 | 0.05 (0) | 0.06 (3) | 0.06 (2) |
| 9-1 | Citrate (Na3-Citrate) | HCl | 3.13, 4.76, 6.4 | -0.0024, -0.0016, 0.0005 | 0.5 | 4.0 | 0.0 | 114 | 0.03(0) | 0.05(10) | 0.05 (9) |
| 9-5 | Citrate (Na3-Citrate) | Citric acid | 3.13, 4.76, 6.4 | -0.0024, -0.0016, 0.0005 | 0.5 | 4.0 | 0.0 | 10 | No Exp2 | 0.03 (0) | 0.03 (0) |
| 10-1 | Na-Formate | HCl | 3.75 | 0.0002 | 0.5 | 4.0 | 0.0 | 48 | 0.04 | 0.07 (5) | 0.04 (0) |
| 10-4 | Na-Formate | Formic acid | 3.75 | 0.0002 | 0.5 | 4.0 | 0.0 | 24 | No Exp2 | 0.05 (1) | 0.02 (0) |
| 11-1 | NaH2PO4 | HCl | 2.15, 7.21, 12.33 | 0.0044, -0.0028, -0.026 | 0,46 | 4.0 | 0.0 | 18 | 0.01 (0) | 0.05 (0) | 0.05 (0) |
| 11-2 | NaH2PO4 | NaOH | 2.15, 7.21, 12.33 | 0.0044, -0.0028, -0.026 | 0,46 | 4.0 | 0.0 | 48 | 0.02(0) | 0.16 (12) | 0.10(8) |

Fig 4

Table 1 cont.

| Nr-Titr | Buffer | Titrant | pKa | dpKa/dT | konst | Shell pos | Shell neg | $N_{OK}$ | r.m.s. (Exp1-Exp2) | r.m.s. Calc-Exp1 (Guggenheim & Schindler) | r.m.s. Calc-Exp1 ("Buffalo") |
|---|---|---|---|---|---|---|---|---|---|---|---|
| 11-13 | NaH2PO4 | Na2HPO4 | 2.15, 7.21, 12.33 | 0.0044, -0.0028, -0.026 | 0.46 | 4.0 | 0.0 | 48 | 0.02 (0) | 0.09 (11) | 0.05 (1) |
| 11-11 | NaH2PO4 | H3PO4 | 2.15, 7.21, 12.33 | 0.0044, -0.0028, -0.026 | 0.46 | 4.0 | 0.0 | 9 | No Exp2 | 0.06 (0) | 0.14 (4) |
| 12-1 | Na2HPO4 | HCl | 2.15, 7.21, 12.33 | 0.0044, -0.0028, -0.026 | 0.46 | 4.0 | 0.0 | 48 | 0.02 (0) | 0.10 (13) | 0.05 (1) |
| 12-12 | Na2HPO4 | NaH2PO4 | 2.15, 7.21, 12.33 | 0.0044, -0.0028, -0.026 | 0.46 | 4.0 | 0.0 | 7 | 0.03 (6) | 0.07 (1) | 0.03 (3) |
| 14-2 | Hepes | NaOH | 3.0, 7.56 | 0, -0.014 | 0.5 | 4.0 | 20.0 | 22 | 0.03 (2) | 0.04 (0) | 0.04 (0) |
| 15-2 | Mes | NaOH | 6.21 | -0.008 | 0.5 | 4.0 | 13.0 | 70 | No Exp2 | 0.15 (38) | 0.06 (6) |
| 16-1 | Na2CO3 | HCl | 6.35, 10.49 | -0.0055, -0.009 | 0.5 | 4.0 | 0.0 | 50 | 0.05 (0) | 0.10 (17) | 0.06 (4) |
| 20-1 | Glycine | HCl | 2.35, 9.78 | -0.002, -0.025 | 0.5 | 500 | 4.2 | 25 | No Exp2 | 0.16 (17) | 0.04 (0) |
| 20-2 | Glycine | NaOH | 2.35, 9.78 | -0.002, -0.025 | 0.5 | 500 | 4.2 | 25 | No Exp2 | 0.06 (3) | 0.03 (0) |
| 21-1 | Ethanolamine | HCl | 9.5 | -0.032 | 0.5 | 0.0 | 0.0 | 24 | 0.04 (2) | 0.07 (5) | 0.06 (3) |
| 22-1 | Diethanolamine | HCl | 9.01 | -0.025 | 0.5 | 0.8 | 0.0 | 51 | 0.04 (3) | 0.06 (3) | 0.06 (2) |
| 23-1 | Triethanolamine | HCl | 7.77 | -0.02 | 0.5 | 0.0 | 0.0 | 58 | 0.04 (0) | 0.07 (7) | 0.06 (5) |
| 27-2 | Piperazine-2HCl | NaOH | 5.5, 9.81 | -0.015, -0.026 | 0.5 | 4.0 | 0.0 | 4 | 0.05 (2) | 0.17 (2) | 0.03 (0) |
| 32-2 | Succinic acid | NaOH | 4.20, 5.75 | -0.0018, 0 | 0.5 | 4.0 | 0.8 | 72 | 0.04 (0) | 0.07 (10) | 0.06 (9) |
| 38-2 | MOPS | NaOH | 7.19 | -0.011 | 0.5 | 4.0 | 13.0 | 72 | 0.06 (2) | 0.15 (39) | 0.07 (9) |

Fig 4 cont

PREPARATION OF LIQUID MIXTURES

CROSS-REFERENCE TO RELATED APPLICATIONS

This application is a filing under 35 U.S.C. §371 and claims priority to international patent application number PCT/SE2009/050399 filed Apr. 20, 2009, published on Oct. 29, 2009 as WO 2009/131524, which claims priority to application number 0800915-1 filed in Sweden on Apr. 21, 2008.

FIELD OF THE INVENTION

The present invention relates to a method of generating a liquid mixture of controlled pH and ionic strength, as well as to an apparatus applicable in such a method. The invention is of general interest in any situation where precise buffer preparation is required.

BACKGROUND OF THE INVENTION

Obtaining liquids of precisely known composition is in many cases important, as when buffers having a specified pH and optionally also ionic strength are utilised. Further, in many cases, the composition of the liquid should not only be at each moment precisely known and controlled, but also should vary with time in a precise and controlled manner.

One application where the composition of liquids is of utmost importance is in liquid chromatography, and more specifically when elution i.e. the release of isolated target molecules from the chromatography matrix, is carried out by gradient elution. For example, in ion exchange chromatography, which is a frequently used method for the separation and purification of biomolecules, gradient elution is sometimes used, e.g. for finding the optimal elution conditions enabling the design of an industrial process utilizing stepwise elution. As is well known, the eluent then contains an inert salt and the gradient is performed by varying the concentration of this salt. It is well known that a change in salt concentration i.e. ionic strength also affects the pH, and it has been well documented that the pH and ionic strength of the eluent are the two most important parameters that control selectivity of protein separations on ion exchange resins.

U.S. Pat. No. 5,112,949 (Vukovich) relates to an automated system for performing a separation using a gradient. A problem with such manual and automated systems with gradually changing gradients is that if the gradient is made shallow, then it takes a lot of time to perform the elution and if the gradient is made steep then instead of each biomolecule of interest being eluted in turn the elution of the biomolecules overlap. This leads to several species of biomolecules being collected in each fraction instead of each specie of biomolecule being collected in its own, separate fraction.

U.S. Pat. No. 7,138,051 (De Lamotte) relates to a chromatography system, method and software for the separation of biomolecules. More specifically, this patent relates to optimization of the separation of biomolecules eluted from a chromatography column in which the concentration of a component added to an elution buffer is varied in order to form an elution buffer solution of gradually changing concentration of said added component.

Okamoto (Hirokazu Okamoto et al, Pharmaceutical Research. Vol. 14, No. 3, 1997: Theory and Computer Programs for Calculating Solution pH, Buffer formula, and Buffer Capacity for Multiple Component System at a Given Ionic Strength and Temperature) described computer programs to calculate solution pH, buffer formula and buffer capacity at a given ionic strength and temperature. However, the buffer solutions prepared by Okamoto et al show a pH variation that increase with the increased salt concentration, even at low concentrations such as 0.3 M. Thus, the Okamoto methods are not sufficient to provide buffer solutions of constant pH which also contain salt.

The traditional way of gradient formation has involved the careful preparation of eluents comprising inert salts as well as buffers of predetermined pH to effect the ionic strength gradient at constant pH. The optimization of the separation of the proteins has been accomplished by changing the slope of the inert salt gradient and/or replacing the buffer system by one with a different pH.

In the early prior art, the optimization included the preparation of numerous buffer solutions with predetermined pH and salt concentrations, which had to be meticulously titrated for the separations to be reproducible. Obviously, such methods are both time consuming and awkward.

Methods for the calculation of buffer pH at moderate ionic strengths (up to 100 mM) are documented in the literature and are based on the algebraic or computer based solution of the equations of equilibrium among the various charged and uncharged species present in the buffer solution.

For a particular basic species (which can be a base B or a conjugate base $A^-$) in equilibrium with a corresponding acidic species (which can be a conjugate acid $BH^+$ or an acid HA, respectively) the equilibrium can be written $$H^+ + \text{basic species} \Longleftrightarrow \text{acidic species}^+ \qquad \text{Eq 1.1}$$

The corresponding equilibrium constant $K_a$ is defined as $$K_a = (H^+)(\text{basic species})/(\text{acidic species}^+) \qquad \text{Eq 1.2}$$

wherein the parenthesis denotes the activities of each species. Taking the logarithms of both side of Eq. 1.2 and solving for the pH defined as $-\log(H^+)$ gives $$pH = pKa + \log\{(\text{basic species})/(\text{acidic species})\} \qquad \text{Eq 1.3}$$

which is sometimes known as the Henderson-Hasselbach equation. The reason why the activities are to be used in Eq 1.2 rather than the corresponding concentrations is that due to mainly electrostatic interactions, the ions involved tend to become shielded from the environment. However, whereas pH measurements are direct observations of the activity of the protons, it is rather the concentrations and not the corresponding activities of the buffer ions which are observed for instance by weighting, pippeting or pumping their amounts and volumes. The activity of each ion is related to the corresponding concentration through the activity coefficient $\phi$ $$(\text{species}) = \phi[\text{species}] \qquad \text{Eq 1.4}$$

At the ideal state of infinite dilution, $\phi$ becomes 1 and the activity of every ion become equal to the corresponding concentration. However, in real cases, the ionic strength is different from 0 and the activity coefficients of the different species become less than 1.

A well established model for these deviations has been developed in the so called Debye Hückel theory, known as $$-\log \phi = (AZ^2 I^{0.5})/(1+0.3*10^8 aI^{0.5}) \qquad \text{Eq 1.5}$$

wherein A is a constant, or rather a temperature dependent parameter ~0.51. Using well known data, the value of A can accurately be calculated as $A = 0.4918 + 0.0007*T + 0.000004*T^2$ where T is the temperature in degrees Celsius. Z is the charge of the ion and the quantity a, the radii of the hydrated ions (in Å), is described as the "mean distance of approach of the ions, positive or negative" in the original paper of Debye and Hückel.

In a table presented in the above-discussed article by Kielland, this parameter, also known as the ion size parameter is shown to be different for different ionic species. I is the ionic strength $$I = \frac{1}{2}\Sigma(C_i Z_i^2) \text{ (includes all ions)} \quad \text{Eq 1.6}$$

$C_i$ is the concentration and $Z_i$ is the charge of ion present in the solution (in units of electronic charge).

Inserting Eq 1.4 into Eq 1.3 gives the pH in terms of the concentrations instead of the activities:

$$\begin{aligned} pH &= pK_a + \log\{\varphi_b[\text{basic species}]/(\varphi_a[\text{acidic species}])\} \quad \text{Eq. 1.7} \\ &= pK_a + \log\varphi_b - \log\varphi_a + \log\{[\text{basic species}]/[\text{acidic species}]\} \\ &= pK_a' + \log\{[\text{basic species}]/[\text{acidic species}]\} \end{aligned}$$

where $$pK_a' = pK_a + \log\varphi_b - \log\varphi_a \quad \text{Eq. 1.8}$$

is an apparent $pK_a$ value which allows the use of the measurable values of the concentrations of the different buffer species. The value of $pK_a'$ can be calculated inserting Eq 1.5 into Eq 1.8 giving $$pK_a' = pK_a + (AZ_a^2 I^{0.5})/(1+0.33*10^8 a_a I^{0.5}) - (AZ_b^2 I^{0.5})/(1+0.33*10^8 a_b I^{0.5}) \quad \text{Eq 1.9}$$

where the introduction of the subscripts a and b was necessary to specify the parameters corresponding to the acid and the base respectively. Thus
$Z_a$=Charge of acidic species
$Z_b$=Charge of basic species
$a_a$=ion size parameter of the acidic species
$a_b$=ion size parameter of the acidic species Applied to pH calculations, the Debye-Hückel theory results in the modification of the $pK_a$ values of the buffers (known as the thermodynamic pKa values) into corresponding $pK_a'$ values given by Eq 1.9. Most of the parameters in Eq 1.9 are straight forward to estimate. The most challenging parameter is a.

Guggenheim & Schindler (see Guggenheim E A & Schindler T D. (1934) *J. Phys. Chem.* 33. 533), has suggested an approximation of the parameter a set to 3 Å for all buffer molecules leading to the somewhat simplified formula $$pK_a' = pK_a + (AZ_a^2 I^{0.5})/(1+I^{0.5}) - (AZ_b^2 I^{0.5})/(1+I^{0.5}) \quad \text{Eq 1.10}$$

Eq 1.10 above is the formula for ionic strength correction usually found in the literature. Sometimes correction terms are added to the right hand side of this equation to compensate for accuracy loss at higher ionic strengths for various buffers. However, the accuracy obtained by doing this is poor when the ionic strength is as high as 1M, which is within commonly used ranges in gradient elution in for instance ion exchange chromatography and HIC.

Kielland (Jacob Kielland in Activity Coefficients of Ions in Aqueous Solutions, September 1937) has studied activity coefficients of ions in liquids and provides an extended table of ionic activity coefficients, taking into consideration the diameter of the hydrated ions. The data presented by Kielland for the hydrated ion size parameter $a_i$ was obtained using four different models: Bonino's model which takes into account the crystal radius and deformability; the well known equation $108a_i=182z_i/1_\infty$, which takes ionic mobilities into consideration; the empirical modification thereof by Brull, and finally the Ulrich entropy deficiency method. Rounded average values of said four models were used to obtain the data reported in that study. The $a_i$ values presented by Kielland present a substantial variation, from 2.5 to as much as 11, and non-general models are suggested for the activity coefficient based on this variation dependent upon the nature of the ions i.e. one equation for inorganic ions and one different equation for organic ions.

U.S. Pat. No. 6,221,250 (Stafström) relates to a method of preparing liquid mixtures which advantageously utilizes the above-discussed approximation of the parameter a. More specifically, the disclosed method of preparing a mixture comprises the following components: (i) one or more buffering species; (ii) an acid or alternatively a base; (iii) optionally a salt; and (iv) a solvent. The proportions of the components (i) to (iv) are concomitantly varied in such a way as to take account of the interrelationship of the pH and the ionic strength of the liquid mixture to obtain at each moment a preselected pH of the mixture, and the method is based on the use of a modified and repetitive Guggenheim-Schindler (1.10, below) equation wherein buffer specific correction factors are used for attainment of constant pH along a gradient. Thus, in certain situations, a disadvantage of this method can be that if a new buffer needs to be introduced; calculations need to be made again.

Another application where it is essential to prepare liquid mixtures of controlled pH and ionic strength is in high throughput screening (HTS), which is a method for scientific experimentation frequently used in drug discovery but also relevant to the fields of biology and chemistry. Through a combination of modern robotics, data processing and control software, liquid handling devices and sensitive detectors, HTS allows a researcher to effectively conduct millions of biochemical, genetic or pharmacological tests within a short period of time. Through this process one can rapidly identify active compounds, antibodies or genes which modulate a particular biomolecular pathway. The results of these experiments may e.g. provide starting points for drug design and for understanding the interaction or role of a particular biochemical process in biology. Automation is an important element in HTS's usefulness. A specialized robot is often responsible for much of the process over the lifetime of a single assay plate, from creation through final analysis. An HTS robot can usually prepare and analyze many plates simultaneously, further speeding the data-collection process. However, for these robots to function accurately, again the preparation of liquid mixtures such as buffers having precisely controlled pH as well as ionic strength is essential.

One application within the HTS area which is becoming of increasing value is high throughput process development (HTPD), where the roles of pH and the ionic strength are very important as they rule binding behaviour of target(s) and contaminants(s). By successful design of such high throughput processes, the conditions for high mass transfer rates and accordingly process economy, and also for optimal elution and hence highest recovery, can be accurately predicted. However, such successful design would require or at least be much improved by automatic buffer preparation, allowing the preparation of numerous conditions such as pH and I in short time spans.

Another need of precise and well controlled buffer preparation appears in microplates and other labware formats. Many steps in microplate and filter plate based assays are easily parallelized by using e.g. multi-pipettes and vacuum blocks for the processing and plate readers for the detection of results. There is often no need for higher level of automation, i.e. automated transportation of plates. This is valid even for many "throughput applications" since a factor 96 or 384 in the number of experiments is already gained by the plate integration in the first place. However, there are cases involving tedious preparation of individual wells in the plate. While dedicated, small footprint plate readers are taken for granted for the detection and analysis of individual wells there is no similar dedicated, reasonably priced, small footprint solution for buffer preparation in individual wells in one microplate. TECAN is a company which has addressed the problem by writing software to provide buffer preparation in microplates using their lab automation platform. This could at a first glance be perceived as an elegant solution, but results in occupation of an expensive automation infrastructure for hours for a relatively simple task in the well equipped automation lab. Furthermore, a huge investment is required for the small lab to take advantage from the TECAN solution.

Thus, there is also a need of an automatically dispensing device, such as a stand-alone unit, which may be used as a workstation together with automation solutions e.g. to reduce the workload in a primary automation infrastructure.

SUMMARY OF THE INVENTION

One aspect of the present invention is to provide a method of precise and accurate control of the pH and ionic strength of a liquid mixture. In brief, this may be achieved by providing a method of preparing a liquid mixture, such as a buffer, which method takes into account both the size and charge of organic as well as inorganic ions. This can be achieved as defined in one or more of the appended claims.

A further object of the invention is to provide an improved method of buffer preparation, wherein the exact composition is first calculated and the buffer is subsequently prepared in a single step.

A specific aspect of the invention is to provide the tools for buffer preparation wherein there is a guaranteed pH range for each respective buffer by calculation of the buffer capacity.

Another aspect of the present invention is to provide a method of defining the composition of a liquid mixture in terms of buffer species, buffer concentration and/or salt concentration based on a desired pH and/or ionic strength and buffer capacity. Thus, starting from a desired pH of a liquid mixture, and optionally also a desired ionic strength and buffer capacity, the present invention will define the appropriate buffer species as well as appropriate values of buffer as well as salt concentration to obtain said pH and ionic strength and buffer capacity.

Finally, another aspect of the invention is to utilise the present method of buffer definition in an auto-dispensing device for intelligent buffer preparation in microplates and other labware. This can be achieved by introducing software based on the model discussed above. In a specific aspect, the device comprises an interface for automation.

Further aspects and advantages of the present invention will appear from the detailed description and claims that follow.

DEFINITIONS

A "buffer" means herein a component or compound, that in liquid solution maintains a nearly constant pH value despite the addition of substantial quantities of acid and/or base.

The term "computer program" is used herein interchangeably with the term "software".

BRIEF DESCRIPTION OF THE DRAWINGS

FIG. 4 discloses a table 1 showing the root mean squared differences between experimental and between calculated and experimental pH values for three different methods. The methods differ in the type correction to the $pK_a$ value for the ionic strength: Correction according to Guggenheim & Schindler Eq 1.10 and correction according to this method Eq 1.9 with Eq 1.11. The numbers in parenthesis give the number of differences larger than 0.1 pH units. The r.m.s.d. values are also given in pH units. $N_{OK}$ is the number of experiments with buffer capacity at or above 0.01 moles of strong acid/base per pH unit (log β>−2). Shell values in grey have no effect.

DETAILED DESCRIPTION OF THE INVENTION

In a first aspect, the present invention relates to a method of determining the relative component proportions of at least one each of:

a buffer;
an acid or a base;
a solvent;
and optionally
a salt, for providing a liquid mixture of pre-defined pH and ionic strength, wherein the relative component proportions are determined using the equation of Debye-Hückel, wherein the ion size parameter a in the Debye-Hückel equation is determined as the weighted mean ion size of all species contributing to the ionic strength of the liquid mixture, and wherein the ionic strength of each species is used as weighting parameter.

Thus, there is provided a general method applicable to liquid mixtures comprising organic buffer species as well as inorganic species. As discussed above, such buffered liquid mixtures are widely used in many fields of chemistry and biology. The present method allows improved prediction (determination) of relative component proportions in order to achieve a liquid mixture of pre-defined pH and ionic strength, especially at high buffer and/or salt concentrations, which is supported by the experimental results below. It should also be noted that the present method may be used, in the opposite way, to determine the resulting pH and ionic strength of a liquid mixture of a specific constitution.

As discussed above, different approximations of the Debye-Hückel equation are widely used in order to determine relative component proportions for buffer solutions etc., but so far they all provide poor accuracy at higher concentrations of buffer and/or salt. The proposed method overcomes these problems by determining the ion size parameter a as the weighted mean ion size of all species contributing to the ionic strength of the liquid mixture, and wherein the ionic strength of each species is used as weighting parameter.

According to one embodiment, the ion size parameter a for the liquid mixture is calculated as $$a = \frac{\sum I_i a_i}{I}$$ Eq. 1.11 wherein $I_i$ is the ionic strength and $a_i$ the ion size parameter of species i, and I the total ionic strength defined in Equation 1.6 above. Starting from said equation then:

$$I_i = \frac{1}{2} Z_i^2 C_i$$ Eq. 1.12

The ion size parameter $a_i$ of species i is an experimentally established or approximated value, and examples of $a_i$ values for some buffers and salts are listed in table 2 of example 2.

Figure 5:
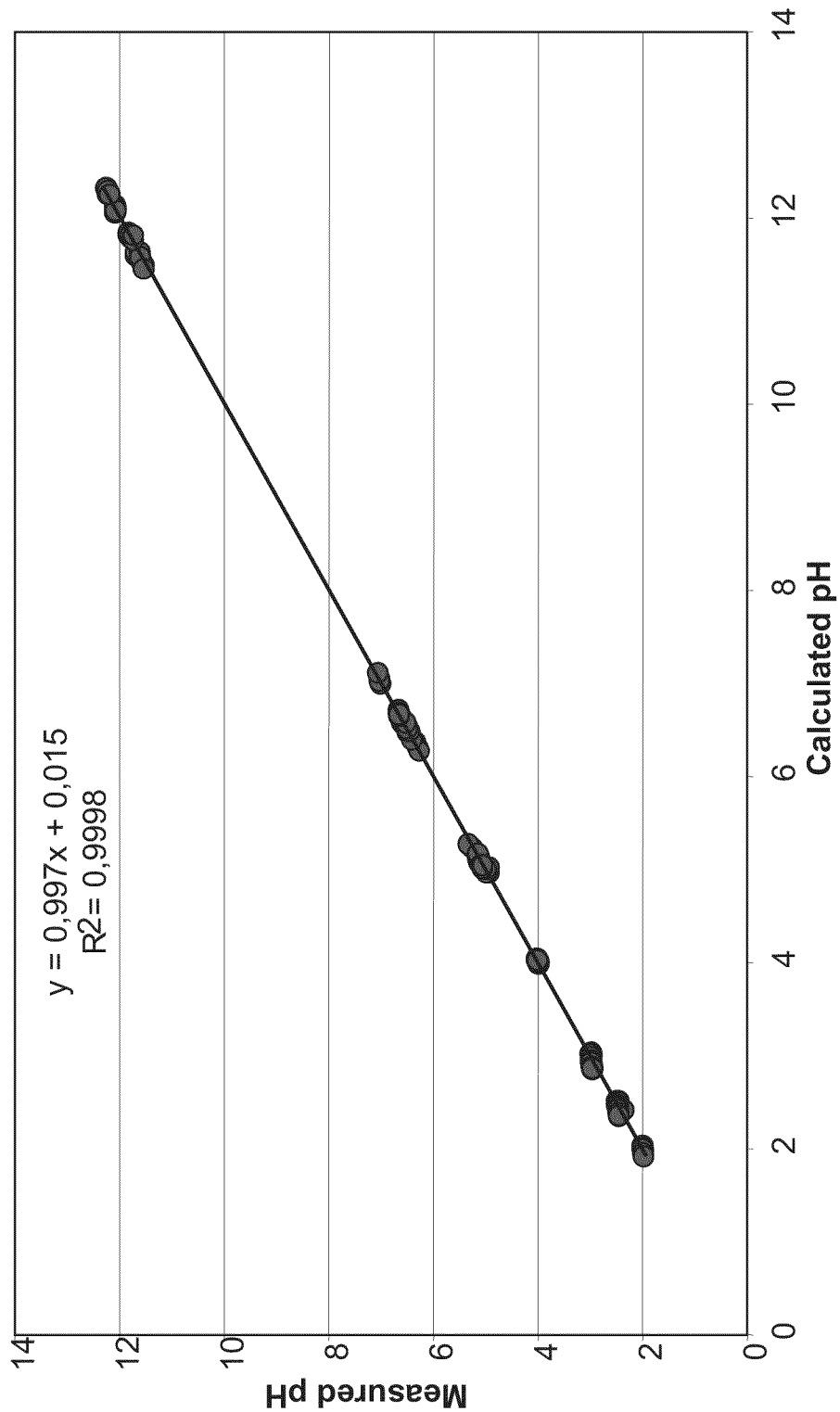
FIG. 5 shows a plot of calculated pH vs. measured pH for a large number of buffer samples.

Throughout this disclosure the term "species" covers any and all ions or molecules that contribute to the ionic strength of the liquid mixture, and more specifically one component, e.g. a buffer system such as a weak acid, may correspond to two or more species of different charge, each with an associated $a_i$ value. Due to the fact that $a_i$ is related to the "ion size" in a specific environment, it has been found that the $a_i$ value of one specific species may be different for different combinations of components, e.g. buffer, salt etc. For example, it has been found that the $a_i$ values for NaCl are different when mixed with a phosphate buffer compared to an acetate buffer, as is shown in table 2 below. However, it has been found that the $a_i$ values are valid for tested component combinations over a wide range of pH and Ionic strengths using the present method, resulting in improved predictability over essentially the whole ranges. FIG. 5 of example 2, shows a plot of calculated pH vs. measured pH for a large number of buffer samples prepared based on the above method. From this plot it is evident that the disclosed method is capable of defining relevant relative component proportions over a very wide pH range.

According to one embodiment it has further been found that the ion size parameter a in the Debye-Hückel equation may be approximated as $$a = 0.5 * (mass)^{1/3} + shell$$ Eq. 1.13 whereby the determination of a requires less processing capacity. In this equation, the term "shell" is motivated by an additional layer, which can be considered a "hydration layer" of the ion. With respect to this embodiment, it was found that if "shell" was set at a specific, fixed value, then the term referred to as "constant" in the Debye-Hückel equation equals 0.5, as appears e.g. from the table 1 presented in FIG. 4.

Thus, in one embodiment, "shell" is fixed at a specific value for a positively charged ionic species and "shell" is fixed at another, different value for a negatively charged ionic species. In an one embodiment, "shell" is in the range of 3.8-4.2, such as 3.9-4.1 or 4, for a positively charged ionic species (shellpos=4). In another specific embodiment, "shell" is in the range of 0-0.2, such as 0-0.1 or 0, for a negatively charged ionic species (shellneg=0).

An advantage of the present invention, as compared to prior art methods such as the above-discussed Okamoto, the present invention enables the preparation of liquid mixtures such as buffers not only at low salt concentrations but also at higher salt concentrations such as above 1M, above 2M or even above 5M.

Thus, in a specific embodiment, the present invention is a method of providing a liquid mixture such as a buffer wherein the salt concentration is up to 1M, specifically in the range of 1-2M or more specifically above 2M.

According to one embodiment, the relative component proportions are determined using an iterative procedure.

Figure 1:
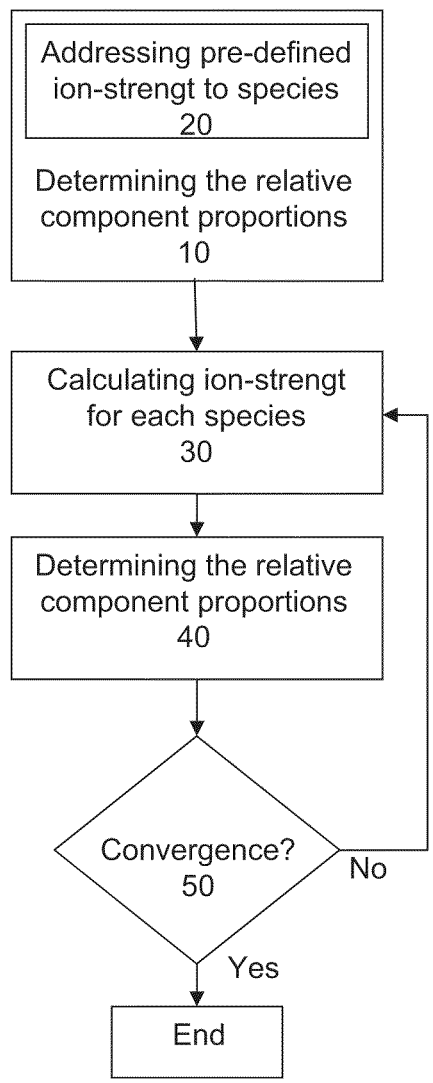
FIG. 1 schematically shows the steps of a method for providing a liquid mixture of pre-defined pH and ionic strength.

According to one specific embodiment, schematically shown in FIG. 1, the iterative procedure comprises:
(a) determining 10 the relative component proportions wherein the pre-defined ionic strength of the liquid mixture is addressed 20 to the species according to a pre-defined distribution among the species;
(b) on the basis of the relative component proportions determined in the preceding step, calculating 30 the ionic strength of each species in the mixture;
(c) determining 40 a new set of relative component proportions; taking account of the ionic strength calculated in (b), and
(d) repeating the steps (b) and (c) until a predetermined convergence criteria is met 50.

The addressing of the pre-defined ionic strength of the liquid mixture among the species, in step (a), is pre-defined to achieve a suitable starting point for the iterative process in order to achieve quick convergence and to avoid false convergence. According to one embodiment the pre-defined ionic strength of the liquid mixture is addressed to the salt species, as they normally are dominant contributors to the total ionic strength of a buffer comprising a salt component. For liquid mixtures, without any salt component, the pre-defined ionic strength of the liquid mixture is addressed In step (b), the relative component proportions determined in the preceding step, i.e. step (a) in the first iteration and step (c) in the subsequent iterations, are used to calculate the ionic strength of each species in the mixture. Hence, the concentration of each species as defined by the relative component proportions is used to calculate a more correct ionic strength distribution, which subsequently is used to determine more correct relative component proportions (step (c)) and so on until convergence.

The predetermined convergence criteria may be selected to be any suitable criteria that ensure that the relative component proportions are defined with sufficient accuracy, at a reasonable computational effort. According to one embodiment, the convergence criteria may be selected to be the iteration step when the deviation between the last set of relative component proportions and the set found in the immediately preceding step does not exceed a predefined maximum level, this last set of relative component proportions then being retained as yielding the mixture of the selected pH at the given salt concentration. In alternative embodiment, the convergence criteria may e.g. be selected as a fixed number of iterations, or other suitable relations. In a specific embodiment, the procedure above is iterated less than 10 times, preferably less than 8 times and more preferably 4-6 times, such as 5 times.

Figure 2:
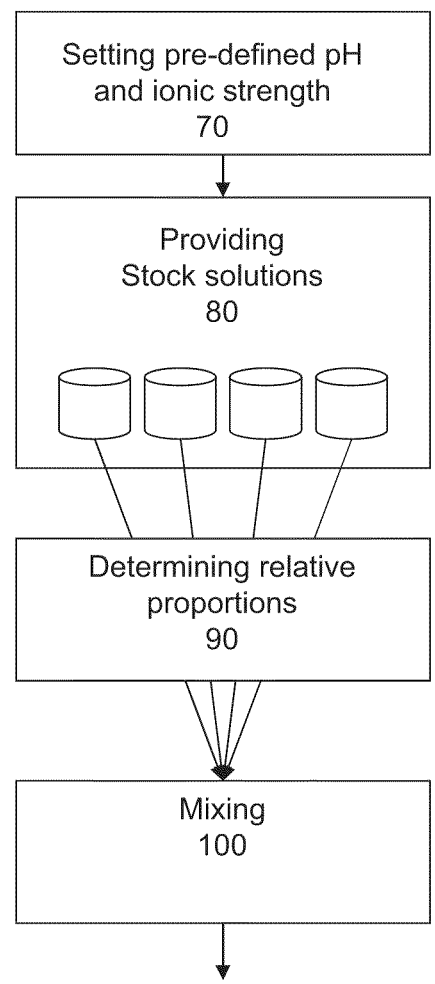
FIG. 2 discloses one embodiment of the buffer preparation according to FIG. 1 done through a four-inlet fast switching valve. Buffer titration can be done both with corresponding or strong acid/base. Actual buffer mixing ratios are displayed by the software, in this case a specifically modified version of UNICORN™ (GE Healthcare). A stable pH of prepared solutions is obtained independent of ionic strength and temperature. There is an automatic check of buffer capacity. Buffer concentration and pH is possible to set in method. The quaternary valve will open one port for a short time and then open the next port and so on. The different stock solution volume segments will be mixed completely in the mixer to form the buffer of choice. The opening time is controlled by an algorithm to get the correct pH. The actual proportions used during a run is displayed as percentage in curves Conc Q1 through Q4 in System Control as well as in Evaluation in UNICORN™.

According to one embodiment, schematically shown in FIG. 2, the method of determining the relative component proportions of a liquid mixture may be used to in a method for providing a liquid mixture of pre-defined pH and ionic strength 70, comprising:
  providing 80 component stock solutions of at least one each of
    a buffer;
    an acid or a base;
    a solvent;
    and optionally
    a salt,
  determining 90 the relative proportion of each component stock solution to be mixed using the above method,
  mixing 100 the stock solutions.

In alternative embodiments, one or more component stock solutions may be substituted by a solid phase stock source of said component, whereby the relative proportion of the solid phase is dissolved upon mixing of the components.

By this method, a large range of buffer solutions or other liquid mixtures may be prepared with high accuracy, in response to pre-defined pH and ionic strength.

According to one embodiment, the method may be used to prepare liquid mixtures where the ionic strength is gradually changed over time (e.i. over volume) by combining concomitantly varying proportions of the component stock solutions, and wherein the pH value of the liquid flow may be maintained substantially the same. If desired, liquid mixtures with pH gradient or even combinations of pH and ionic strength gradients may be prepared.

The present invention is useful to determine relative component proportions for liquid mixtures such as buffers which comprise two or more buffering species, often recognized as multiple buffer species liquids. Thus, in one embodiment, the present invention is a method as discussed above, wherein, two or more stock solutions are prepared which stock solutions comprises different buffering species. In an alternative embodiment, a stock solution comprising at least two, such as three, four or more, buffering species is provided.

In one embodiment, the present method of determining the relative component proportions may be referred to as a method for buffer definition, which defines one or more of the parameters selected from the group consisting of buffer species; buffer concentration; and salt concentration required to obtain a buffer having a desired pH value and/or a desired ionic strength and buffer capacity. In one embodiment, the buffer definition is obtained at one specific point of time. In an alternative embodiment, the present buffer definition is obtained in-line in a continuous process. The method of buffer definition can include one or more of the elements discussed above in the context of the preparation of a liquid mixture.

As discussed above, the liquid mixture prepared using the present method may be a buffer, which is useful in various applications such as high throughput screening applications and in chromatography. In chromatography the liquid prepared according to the present method is advantageously the eluent, which accordingly will comprise a gradually changing ionic strength, also known as a salt gradient. Such a gradient may be increasing or decreasing.

In another aspect, the present invention relates to a computer program capable of carrying out the calculations described above.

According to a specific embodiment, there is provided a computer program for determining the relative component proportions of at least one each of:
  a buffer;
  an acid or a base;
  a solvent;
  and optionally
  a salt,
for providing a liquid mixture of pre-defined pH and ionic strength in accordance with the above method of determining the relative component proportions, wherein the determined component mixing proportions are displayed to a user for evaluation, and/or used for controlling a liquid mixer device.

The computer program according to the invention, which may be presented on a memory device such as a disk or a stick; or as part of a control device, is useful for automated preparation of liquid mixtures, preferably liquid flows, having controlled pH and ionic strength.

In one embodiment of a computer based implementation of the method of determining the relative component proportions for providing a liquid mixture of pre-defined pH and ionic strength according to above, the ion size parameter $a_i$ for each species is stored in a accessible database, table or the like for use in the calculations. One example of such a table is shown in table 2 with reference to example 2.

In a specific embodiment, the computer program may be run in design mode, which means that the program will calculate the receipt (i.e. amounts of titrant, titrant, water and salt) to achieve a solution of a given pH and ionic strength (alternatively salt concentration instead of ionic strength). In an alternative embodiment, the computer program can be run in pH calculation mode, which means that the program will calculate the pH and the ionic strength obtained when certain amounts of buffer components are mixed.

Figure 3:
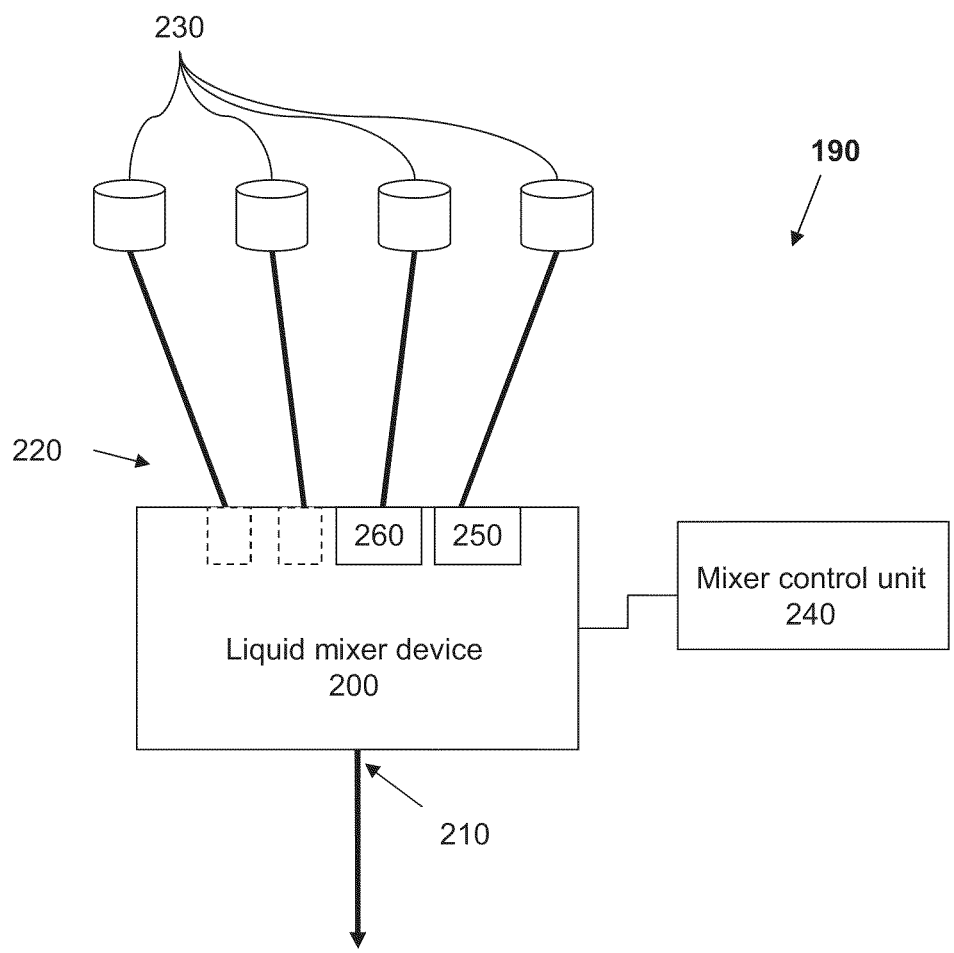
FIG. 3 schematically shows a buffer preparation device.

In a third aspect, schematically shown in FIG. 3, there is provided a buffer preparation device 190, comprising:
  a liquid mixer device 200 comprising a mixed liquid outlet port 210, and a plurality of inlet ports 220 connected to component sources 230 of at least one each of:
    a buffer;
    an acid or a base;
    a solvent;
    and optionally
    a salt,
  a mixer control unit 240 arranged to control the relative component proportions supplied through the inlet ports of the mixer device providing a liquid mixture of pre-defined pH and ionic strength at the outlet port, the mixer control unit being arranged to determine the relative component proportions using the equation of Debye-Hückel, wherein the ion size parameter a in the Debye-Hückel equation is determined as the weighted mean ion size of all species contributing to the ionic strength of the liquid mixture, wherein the ionic strength of each species is used as weighting parameter.

According to one embodiment, the buffer preparation device comprises one or more controllable valves 250, pumps 260 or the like for supplying the relative proportions of associated components to the mixer device. In the disclosed embodiment, a valve 250 and a pump 260 are schematically shown as being integrated in the liquid mixer device, but alternatively they may be provided as separated components.

According to one embodiment, the buffer preparation device is integrated as apart of a liquid chromatography system. Thus, the buffer preparation device is advantageously used in chromatography as discussed in detail in the above-discussed U.S. Pat. No. 6,221,250, which is hereby included herein via reference.

In one specific embodiment, the buffer preparation device comprises a multiport inlet valve, such as a 4-inlet fast switching valve; means for buffer titration; a display of actual buffer mixing ratios; means for maintaining the pH independent of ionic strength and temperature; means for automatic check of buffer capacity. The quaternary valve will open one port for a short time and then open the next port and so on. The different stock solution volume segments will be mixed completely in the mixer to form the buffer of choice. The opening time is controlled by an algorithm to get the correct pH.

Buffer titration can be done both with corresponding or strong acid/base. Actual buffer mixing ratios may be displayed and/or controlled by a software, such as modified version of UNICORN™ (GE Healthcare). A stable pH of prepared solutions is obtained independent of ionic strength and temperature. There may be an automatic check of buffer capacity. Buffer concentration and pH possible to set in method.

In still another aspect, there is provided a robotic liquid handler which provides a liquid flow wherein the pH is maintained substantially the same while the ionic strength is changed. A robotic liquid handler according to this embodiment may be used e.g. in controlling the buffer composition in high throughput screening procedures; in quality control; in DNA quantitation and normalization; in PCR etc. In an advantageous embodiment, the present robotic handler constitutes a part of a system that allows fully automated buffer preparation in 96 well format for high throughput process development. In such system, the computer program according to the invention provides output design in a format that is readily imported into the robotic device.

Finally, the invention also relates the use of the method of determining the relative component proportions discussed above in an auto-dispensing device for intelligent buffer preparation, such as in microplates or other formats, and possibly other labware. One advantage of the method according to the invention is in the accuracy of the pH predictions at ionic strength values as high as 1M or above. In one embodiment, the method is especially for buffer systems with positively charged buffer ions. A stand alone buffer preparation device according to the invention may be used in any lab involved in chemical, biological, biochemical, medicinal research and development for applications like high throughput process development, screening for crystallization conditions, screening for binding conditions etc. and in general any application which requires parallelized buffer preparation in the μl-ml scale. Depending on the software included, the device could easily be tailored also for other applications in need for the same unit operations.

EXAMPLES

The examples below are given for illustrative purposes only, and should not be construed as limiting the invention as defined by the appended claims.

Example 1

Software Development

Materials/Investigated Units

All programming was carried out in a personal computer with a Pentium 4 processor and windows XP operating system.

Methods

In the first part of the development work, version 5 of Borland's C++ Builder was used and later version 4.2 of Visual C++ compiler was used.

Criteria for Acceptance

At the start of this experiment, it was decided that the method should give the right pH with an accuracy of 0.2 pH units. Since the specification of the pump and valve system used is 0.5%, and a normal stock concentration would be 0.2 M, given a minimum buffer capacity[1] of 0.01 (see below) about 0.1 would correspond to the accuracy of the proportioning and 0.1 to the accuracy of the algorithm. The minimum buffer capacity was taken as buffer capacity is defined as |dn/dpH|, where do is the (small) change in amount (in mols) of strong acid/base giving rise to a (small) change dpH in pH. The accuracy of the algorithm was estimated by comparison to experimental pH measurements of buffer solutions. Pippeting errors were estimated at the beginning of the experiment phase and they were considered very small as compared to other errors related to experimental pH determination (data not shown). The experimental error was therefore estimated by measuring the pH of each buffer sample using two different pH meters, with different types of electrodes, giving rise to two different pH values, herein denoted pHExp and pHExp1. The root-mean squared error (r. m. s. e.) was calculated for each experimental series (data set) according to the following formula $$r.m.s.e. = Sqrt(\Sigma(pHExp-pHExp1)^2/N_{OK}) \qquad \text{Eq. 2.1}$$

where the sum is taken for those pH values with a corresponding buffer capacity larger than 0.01 and where $N_{OK}$ is the number of such cases (only results for which the logarithm (base 10) of the buffer capacity ($\beta$) is larger than −2 are taken in consideration). If the r. m. s. e. was found to be larger than 0.05 pH units, then at least one half of the data set (corresponding to one pH meter) was rejected in which case the data set which was more consistent with the established values of buffer constants (pKa and temperature dependence of pKa) found in the literature was kept and used for optimisation of the ionic strength compensation parameters. Even the consistent half of the data set could be rejected in case there was another data set which was consistent with the established values of buffer constants from the literature. The value 0.01 (log −2.0) as a lower limit for the buffer capacity was derived experimentally as it was observed that below this limit the r. m. s. e. increased over 0.05 for most buffer systems (data not shown). As a comparison the corresponding value used in the above discussed U.S. Pat. No. 6,221,250 (Stafström) was 0.0063 (log −2.2). No reference to a "normally accepted value" was found in the literature.

Results

The program "Buffalo" was written in Visual C++ and can be run in Windows for the accurate calculation of buffer pH at ionic strengths as high as 1M.

Structure of the Program

The program "Buffalo" can be run in two modes: design mode and Calc_pH mode. The design mode is used for design of experiments and for the calculation of theoretical titration curves which can be used before the design of experiments to determine an appropriate pH range. The Calc_pH mode is used for parameter optimisation given a set of paired pH measurements. Inputs to the program in both modes are the buffer volume (buff_vol), the temperature (TT), the buffer concentration (buff_conc), the salt concentration (salt_conc), the buffer substance (buff_choice) and the titrant substance (titrate_choice). In addition to this, in design mode the desired pH (pH) is required as input whereas in Calc_pH mode the experimental pH (pHExp), the corresponding replicate (pHExp1), and the number of mols of titrant used in the experiments (titrate_mol_exp) are required. Moreover, in both modes, it is possible to consider a mixture of a number (n_buffs=1, 2 or 3), of buffers buff_choice(1), buff_choice(2), buff_choice(3) instead of a buffer consisting of a single buffer substance (the program has been implemented for a maximum number of three buffer substances but it could easily be modified to include more). This being the case the corresponding buffer concentrations should be provided buff_conc(1), buff_conc(2), buff_conc(3).

Monoprotic vs Polyprotic Buffers

The pH of a monoprotic buffer can be predicted with the Henderson-Hasselbach equation (Eq 1.3 or Eq 1.7)

The concentrations of the basic and acidic species are determined by the buffer concentration and the titrant concentration. Given these and the $pK_a$ of a monoprotic buffer the pH can be derived (corresponds to Calc_pH mode), alternatively, given a desired pH and the buffer concentration the amounts of mol of titrant can be derived (corresponds to design mode). A complication arises as many used buffers are polyprotic i.e. their buffer molecules can accept and give away more than one proton corresponding to more than one $pK_a$ values. The number of species in such a buffer system is always one more than the number of $pK_a$ values (nr_of_pKa). To simplify the implementation of the program, a general model for a tritropic buffer was implemented (an extension to even more $pK_a$ values should be straight forward but not trivial and has to be implemented). Four protonation states or species (s1, s2, s3, and s4) are defined however the parameter nr_of_pKa (which can be 1, 2, or 3) limits the calculations so that for a monoprotic buffer for example, s1 corresponds to the acidic species, s2 to the basic species ant the concentrations of s3 and s4 are set to 0.

Differences and Similarities Between the Two Modes

The two modes work using essentially the same method namely to solve for the amount of mols of titrant necessary to obtain a given pH at a given buffer concentration. Before doing that it is necessary to solve the amount of mols of buffer in each one of the possible number of protonation states (or species). The difference between the modes is that in design mode the procedure is done only twice (kmax=2): one time for the desired pH and the other for pH+pH_step (see below) in order to numerically estimate the buffer capacity. The amount of mols of titrant obtained for the desired pH is then the output of design mode. In Calc_pH mode on the other hand the procedure is repeated across the entire pH scale (1-13, kmax=2600), the pH value that yields the amount of mols of titrant that agrees best with the amount of mols of titrant used in the experiment is the calculated pH value. The pH_step (0.005) limits the accuracy of the pH and buffer capacity calculations. It was found advantageous to use the same algorithm in both modes as errors and unnecessary discrepancies were minimized in this way.

The Equilibrium Equations

The calculation of the amount of mols in each of the protonation species is equivalent to solving the equilibrium equations of each of the species with the "neighbouring" species with one more and/or one less proton and with the concentration of hydrogen atoms (the pH). In other words three equations (corresponding to three pKa values) derived directly from Eq 1.7.

$$xx[i]=10^{(pH-pKaprime[i])} \quad \text{Eq 3.1}$$

where each i corresponds to each pKa(i) value (i=1,2,3), and xx[i] are the ratios between the concentration of the corresponding base and the corresponding acid i.e. $xx[1]=[s_2]/[s_1]$, $xx[2]=[s_3]/[s_2]$, $xx[3]=[s_4]/[s_3]$.

In addition to these three equations, an equation arises because of the conservation of mass $$[s_1]+[s_2]+[s_3]+[s_4]=\text{buff\_conc} \quad \text{Eq 3.2}$$

and the conservation of charge $$[H^+]-[OH^-]+\Sigma\text{spec\_chrg}(s_i)-\text{titrant\_charge\_[titrant]}-\text{spec\_chrg(start\_species)}*[\text{start\_species}]=0 \quad \text{Eq 3.3}$$

By start species it is meant the species of the buffer substance before mixing i.e. the protonation state of the buffer in the can or stock solution. This protonation state is determined by the amount of counterions per buffer molecule because the macroscopic object, can or stock solution has to be electrically neutral. The minus sign in front of [OH$^-$] is due to the minus sign of the charge of the OH ions whereas the minus sign in front of the two last terms is due to the charge of the counterions of the titrant and the start_species respectively.

Finally the water dissociation equilibrium $$[OH^-][H^+]=10^{-14} \quad \text{Eq 3.4}$$

Equations 3.1-3.4 imply that there are six equations with six unknowns (the four $[s_i]$, [OH$^-$] and [H$^+$]) for the case of 3 $pK_a$ values. In the way the solution is implemented here the pH is assumed to be known and thereon [H$^+$] and through Eq 3.4 even [OH$^-$] and it is instead the titrant concentration which is to be solved. The five remaining equations correspond to five unknowns (the four $[s_i]$ and [titrant])

Calculation of the Amount of Mols of Titrant

Once the concentrations of each species $[s_i]$ at equilibrium are known the titrant concentration can be solved using Eq 3.3. There are two cases to consider depending on the type of the titrant, strong acid/base and corresponding acid/base. However, independently on which case it is, solving for the titrant concentration in Eq 3.3 gives $$[\text{titrant}]=(-[H^+]+[OH^-]-\Sigma\text{spec\_chrg}(s_i)*[s_i]+\text{spec\_chrg(start\_species)}*[\text{start\_species}])/\text{proton\_step} \quad \text{Eq 3.10}$$

where $$\text{proton\_step}=-\text{titrant\_charge(strong acid/base)} \quad \text{Eq 3.11a}$$

or $$\text{proton\_step}=\text{spec\_charge(start\_species)}-\text{titrant\_charge (corresponding acid/base)} \quad \text{Eq 3.11b}$$

In other words the parameter proton_step is −1 for HCl and +1 for NaOH, in the case of a weak acid or base titrant the proton_step of the titrant depends on the start species of the buffer according to equation 3.11b or the following equivalent equation $$\text{proton\_step}=\text{titr\_species}-\text{start\_species} \quad \text{Eq 3.12}$$

This procedure is repeated as many times as there are buffer components and the final titrate_mol is the sum of the amount of mols of titrant from each component (see below).

In most of the cases (pH between about 3.5 and 10.5), the contribution of [$H^+$] (at low) or [$OH^-$] (at high pH values) to the charge balance is negligible and can be set to zero in Eq 3.10.

Choice of Titrant

The titrant can be strong (HCl or NaOH). The only difference between these two is in the sign of the number of protons they contribute with. In addition, the titrant can be weak in which case the titrant protonation state (in the can or stock solution) should be provided. Alternatively, the number of acidic protons can be given. The relation between the two is $$\text{titr\_species} = Nr\_of\_pKa + 1 - Nr\_of\_Acidic\_Protons \qquad \text{Eq 3.13}$$

Ionic Strength Iteration Loop

As the ionic strength is calculated from the concentrations of all ions it is necessary to know these concentrations before the ionic strength is accurately computed. However these concentrations are themselves output from the solution of the equilibrium equations which require pKaprime[$i$] which in turn are calculated from the pKa (so called thermodynamic pKa values at 25° C. and 0 ionic strength), the temperature and the ionic strength. Therefore it was necessary to implement an iterative procedure. In the first stage of such procedure, the ionic strength is simply set equal to the salt concentration. In the second iteration step, the ionic strength obtained from the first cycle is used etc. This procedure was found to converge very rapidly. For instance it was found that five iterations was far more than enough to obtain desired accuracy (data not shown). The number of iterations was therefore set to 5 for all cases.

Separate Charges in the Calculation of the Ionic Strength

It was found that the calculation of the ionic strength for ions with more than one charge and where the charges were well separated (as in the case of the citrate ions with 4 and 5 carbon atoms in between the charges) a significantly better accuracy was obtained if the charges were considered as separate instead of as a single point charge. This lead to the introduction of a flag variable separate_charges which was set true for citrate and false for all other buffers considered.

Loop Over Number of Buffer Components, Buffer Parameters

For each buffer species, the following parameters are required. The mass of the buffer substance (Mbuff), the number of pKa values (No of_pKa), the pKa values (pKa[$i$]), the values of the temperature dependence of each pKa value (dpKadT[$i$]), the charge of the most basic form (bc), and the buffer protonation state (start_species) in the can or stock solution. Alternatively, the number of acidic protons can be given. The relation between the two is $$\text{start\_species} = Nr\_of\_pKa + 1 - Nr\_of\_Acidic\_Protons \qquad \text{Eq 3.14}$$

Besides these, the ionic strength correction parameters (konst, shellpos and shellneg) are required.

The total number of mols of titrant (titrate_mol) is equal to the sum of the number of mols of titrant necessary for each buffer component in order to establish equilibrium at the desired pH and this loop is used to calculate this sum. Other sums that are calculated during the loop are the number of counterions of each of the buffer components and also each component's contribution to the ionic strength at equilibrium.

Loop Over Different Protonation States, Temperature Correction of pKa

For each protonation state each of the following are calculated: the charge (spec_chrg[$j$]), the square of the charge (qsq[$j$]), the shell (shell[$j$]), constant (konst[$j$]) and the temperature-corrected pKa value (pKaT[$j$]). The latter is calculated according to the following formula $$pKaT = pKa[i] + (TT - 25) * dpKadT[i] \qquad \text{Eq 3.15}$$

where TT is the temperature in degrees Celsius. The part aaa[$i$] of the ions size parameter a which is dependent only on the mass (we can call it the non-hydrated radius aaa[$i$])

$$aaa[i] = konst[i] * (Mbuff)^{1/3} \qquad \text{Eq 3.16}$$

is also calculated.

Loop Over pKa Values, Calculation of pKa'

The activity coefficients (or rather their logarithms) of the acidic and basic species corresponding to each $pK_a$ value are calculated according to the following formula.

$$\log fi\text{Base} = -A * (qsq[i+1]) * rootI/(1 + 0.33 * (aaa[i+1] + shell[i+1]) * rootI) \qquad \text{Eq 3.17a}$$

$$\log fi\text{Acid} = -A * (qsq[i]) * rootI/(1 + 0.33 * (aaa[i+1] + shell[i+1]) * rootI) \qquad \text{Eq 3.17}$$

Where rootI is the square root of the ionic strength. The parameter a from equation 1 corresponds to the quantity aaa[$j$] + shell[$j$].

From these activity coefficients the pKaprimes are calculated as $$pKaprime[i] = pKaT + \log fi\text{Base} - \log fi\text{Acid} \qquad \text{Eq. 3.18}$$

Influence of [$H^+$] and [$OH^-$] on the Charge Balance

At very low and very high pH values, the contribution of [$H^+$] (at low) or [$OH^-$] (at high pH values) to the charge balance is no longer negligible. Therefore, the possibility to include a correction to titrate_mol due to [$H^+$] and [$OH^-$] was implemented in version 5.07 and later especially as discrepancies between calculated and measured values were consistently observed for phosphate buffer in the low pH range (below 2.5). This was implemented so that at the amount of mols of titrant was corrected at the end of the loop over number of buffer components by adding two terms $$-10^{\wedge}-\{pH\}/(proton\_step*buff\_vol)$$

to electrically neutralize [$H^+$] and $$+10^{\wedge}\{pH-14\}/(proton\_step*buff\_vol)$$

to electrically neutralize [$OH^-$].

Comparison of the Calculated Values with the Experimental Values

A total of 31 buffer systems (combinations of titrand and tirant) are reported here. About 2100 experiments have been carried out of which 817 been rejected due to the rejection criteria (section 2.3). Strong acid/base as well as corresponding acid/base titration have been carried out as well as two buffer mixtures. The list of buffer systems which are not mixtures are reported in FIG. 4 Table 1. The error statistics of the results of the application of this method (program Buffalo version 6.00) as compared to the Debye-Hückel formula interpretation according to Guggenheim & Schindler (Eq 1.10) and also compared to the experimental differences are also presented in the table. In all cases shown in the table the correction due to the contribution of [$H^+$] and [$OH^-$] (section 3.13) has been included. Only in the cases where low pH is considered does this correction produce a significant improvement of accuracy. In the remaining cases the difference is negligible.

Only results for which the logarithm (base 10) of the buffer capacity (β) is larger than −2 from non-rejected data are presented. As an estimate of the experimental error, the root-mean squared error (r. m. s. e.) (eq 2.1) from two measurements of the same buffer mixture according to two different pH meters is also included.

Buffer Mixtures

Two mixtures were considered. A mixture for cation exchange chromatography (pH 2.5-7.2 CIEX) and a mixture for anion exchange chromatography (pH 5.3-9.5 AIEX)

The AIEX mixture (AIEX-mix) was made by mixing 0.1 M Tris and 0.1 M Bis-Tris. The pH range tested was 5.3-9.5. The first data set consisted of single pH measurements. The r. m. s. e. for a second AIEX data set was 0.08 so than one of its series was rejected.

The results for the first data set and the non-rejected series of the second was 1 of 27 possible values outside 0.1 limits (r.m.s.d. 0.06) for this method as compared to 10 out of 27 possible violations for the ionic strength correction due to Guggenheim & Schindler (r.m.s.d. 0.10).

The CIEX mixture (CIEX-mix) was made by mixing 0.0375M Na2HPO4, 0.0125 Na-FORMATE and 0.025M Na-ACETATE. The pH range tested was 2.5-7.2. The experimental r.m.s.e was 0.02 with 0 out of 104 possible (NrOK) differences larger than 0.1. The result of the pH calculations was 4 of 104 possible values outside 0.1 limits for this method (r.m.s.d. 0.05) as compared to 36 out of 102 possible violations for the ionic strength correction due to Guggenheim & Schindler (0.1).

Example 2

Materials/Investigated Units

As in Example 1.

Methods

Version 4.2 of visual C++ compiler was used.

Results

The program "Buffalo Plus" was written in Visual C++ and can be run in Windows for the accurate calculation of buffer pH at ionic strengths and buffer concentrations as high as 1M for the following buffer systems: Phosphate, Citrate, Acetate and Tris.

Structure of the Program

As for Example 1 with one addition: The program can also be run in a third mode "Optimize parameters" which is used to simultaneously optimize parameters (radii of the different charged species of each buffer system) using the Newton Raphson method.

Monoprotic vs Polyprotic Buffers

As in Example 1.

Differences and Similarities Between the Modes.

As for Example 1 but the Calc_pH and Optimize parameters modes kmax=3.

Choice of Titrant

As in Example 1.

Ionic Strength Iteration Loop

As in Example 1,

Loop Over Number of Buffer Components, Buffer Parameters

As in Example 1.

Loop Over pKa Values, Temperature Correction of pKa and Calculation of pKa'

The activity coefficients (or rather their logarithms) of the acidic and basic species corresponding to each pKa value are calculated according to the following formula $$\log fi\text{Base} = -A(qsq[i+1]) * \text{root}I/(1 + 0.33 * \text{ion\_rad} * \text{root}I)$$

$$\log fi\text{Acid} = -A(qsq[i]) * \text{root}I/(1 + 0.33 * \text{ion\_rad} * \text{root}I)$$

where rootI is the square root of the ionic strength. qsq[i] and qsq[i+1] are the square of the charge of the acid and the base respectively corresponding to the pKa value.

$$pKaT = pKa[i] + (TT - 25) * dpKadT[i]$$

where TT is the temperature in degrees Celsius and dpKadT[i] is the temperature coefficient for the pKa value under consideration pKa[i].

$$pKa\text{prime}[i] = pKaT + \log fi\text{Base} - \log fi\text{Acid}$$

The Equilibrium Equations

As in Example 1.

Calculation of the Ion Size Parameter

This is calculated as described as the ionic strength weighted average of the radii of each species. Table 2 shows established ion size parameters $a_i$ for species in of the phosphate, citrate and acetate buffer systems and associated ion size parameters $a_i$ for NaCl. In table 2, only ion size parameters for charged species are listed, and "ion size 2" refers to the ionic species of lowest charge. Consequently "ion size 1" would refer to the non ionic species, but as the charge of such species is zero they do not contribute to the total ion size parameter a as discussed above As acetate is a monoprotic acid, there is only one single $a_i$ value listed. As is mentioned above, it has been found that the ion size parameters $a_i$ for at least some salts e.g. NaCl is dependent on the buffer system which is shown in table 2.

TABLE 2

|  | Ion size 2 | Ion size 3 | Ion size 4 | Ion size Na | Ion size Cl |
|---|---|---|---|---|---|
| Acetate | 18.989 | — | — | 2.42126 | 0.241586 |
| Citrate | 3.13131 | 7.62849 | 6.37154 | 1.00106 | 3.13131 |
| Phosphate | 1.64846 | 6.25134 | 7.91443 | 1.64026 | 1.09941 |

Calculation of the Amount of Mols of Titrant

As in Example 1.

Influence of [H+] and [OH−] on the charge balance

As in Example 1.

Comparison of the Calculated Values with the Experimental Values

FIG. 5 shows a plot of 155 pH measurement versus corresponding predicted values calculated using Buffalo Plus. The buffer systems investigated include phosphate, citrate and acetate.

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. A method for use with a system, the method comprising:
   combining, by the system, a plurality of liquids to create a liquid mixture having predetermined pH and ionic strength, the combining including:
       determining, by the system, the ion size parameter a in the Debye-Hückel equation based on the weighted mean ion size of all species contributing to the ionic strength of the liquid mixture, the ionic strength of each species being used as a weighting parameter in the Debye-Hückel equation;

determining, by the system, the relative component proportions of at least one of each of a buffer, an acid or a base, a solvent, and optionally a salt, based on the Debye-Hückel equation and the determined ion size parameter a; and mixing, by the system, the components according to the determined relative component proportions to obtain the liquid mixture.

2. The method of claim 1, wherein the relative component proportions are determined using an iterative procedure.

3. The method of claim 2, wherein the iterative procedure includes:

(a) determining the relative component proportions wherein a predefined ionic strength of the liquid mixture is addressed to the species according to a predefined distribution among the species;

(b) on the basis of the relative component proportions determined in the preceding step, calculating the ionic strength of each species in the mixture;

(c) determining a new set of relative component proportions;

taking account of the ionic strength calculated in (b), and (d) repeating the steps (b) and (c) until a predetermined convergence criteria is met.

4. The method of claim 3, wherein, in step (a), the predefined ionic strength of the liquid mixture is addressed to the salt.

5. The method of claim 1, wherein the ion size parameter a of the Debye-Hückel equation is determined as $$a = \frac{\sum I_i a_i}{I}$$

wherein $I_i$ is the ionic strength and $a_i$ of species i, and I the total ionic strength.

6. The method of claim 1, wherein the ion size parameter a in the Debye-Hückel equation is approximated as $a = 0.5*(mass)^{1/3}+shell$.

7. The method of claim 6, wherein "shell" is fixed at one value for a positively charged species and fixed at a different value for a negatively charged species.

8. The method of claim 6, wherein "shell" is fixed at a value in the range of 3.8-4.2, for positively charged ionic species.

9. The method of claim 6, wherein "shell" is fixed at a value in the range of 0-0.2 for negatively charged ionic species.

* * * * *